United States Patent [19]

Przybylowicz et al.

[11] 3,992,158

[45] Nov. 16, 1976

[54] INTEGRAL ANALYTICAL ELEMENT

[75] Inventors: Edwin P. Przybylowicz; Allan G. Millikan, both of Webster, N.Y.

[73] Assignee: Eastman Kodak Company, Rochester, N.Y.

[22] Filed: Jan. 2, 1975

[21] Appl. No.: 538,072

Related U.S. Application Data

[63] Continuation-in-part of Ser. Nos. 388,868, Aug. 16, 1973, abandoned, and Ser. No. 267,849, June 30, 1972, abandoned.

[52] U.S. Cl. .............................................. 23/253 TP
[51] Int. Cl.² .................... G01N 21/24; G01N 33/16
[58] Field of Search .............. 23/253 TP; 195/103.5; 426/87, 88; 116/114 AM, 114 P

[56] References Cited
UNITED STATES PATENTS

| | | | |
|---|---|---|---|
| 2,785,057 | 3/1957 | Schwab et al. | 23/253 TP |
| 3,036,893 | 5/1962 | Natelson | 23/230 R |
| 3,368,872 | 2/1968 | Natelson | 23/253 R |
| 3,526,480 | 9/1970 | Findl et al. | 23/253 TP |
| 3,552,928 | 1/1971 | Fetter | 23/253 TP |
| 3,598,704 | 8/1971 | Dahlqvist | 195/103.5 |
| 3,672,845 | 6/1972 | Verbeck | 23/253 TP |
| 3,802,842 | 4/1974 | Lange et al. | 23/253 TP |

*Primary Examiner*—Robert M. Reese
*Attorney, Agent, or Firm*—R. P. Hilst

[57] ABSTRACT

An integral analytical element capable of use in the analysis of liquids, the element having at least two superposed layers including a spreading layer and a reagent layer, in fluid contact. Optionally, the element can be carried on a support material. The spreading layer, which can be an isotropically porous layer, spreads within itself at least a component of a liquid sample applied to the element, or a reaction product of such component, to obtain a uniform concentration of at least one such spread substance at the surface of the spreading layer which faces the reagent layer. The reagent layer, which is desirably uniformly permeable to at least one dissolved or dispersed component of the liquid sample or a reaction product of such a component, can include a matrix in which is distributed a material that can interact with, for example, an analyte or analyte reaction product to produce a detectable change in the element, such as one detectable by measurement of electromagnetic radiation. In a preferred embodiment, the interactive material can chemically react with an analyte or analyte reaction product to produce a color change in the element. In another preferred embodiment, the sample spreading layer can filter out chemically interfering or other undesirable materials and obtain selective spreading of sample components and/or it can provide a reflective background, often useful in obtaining analytical results.

55 Claims, 4 Drawing Figures

18 SPREADING LAYER
16 FILTERING LAYER
14 REFLECTING LAYER
12 REAGENT LAYER
10 SUPPORT

INTEGRAL ANALYTICAL ELEMENT

This application is a continuation-in-part of U.S. Patent application Ser. No. 267,849, filed June 30, 1972, now abandoned, and U.S. Patent application Ser. No. 388,868, filed Aug. 16, 1973, now abandoned.

BACKGROUND OF THE INVENTION

1. Field of the Invention

Chemical analysis of liquids such as water, foodstuffs like milk, and biological liquids is often desirable or necessary. Various elements to facilitate liquid analyses are known. Such elements have often included a reagent for a substance under analysis, termed analyte herein, which reagent, upon contacting a liquid sample containing the analyte, effects formation of a colored material or another detectable change in response to the presence of the analyte. Such elements include, for example, pH test strips and similar indicators wherein a paper or other highly absorbent carrier is impregnated with a material, chemically reactive or otherwise, that responds to contact with liquid containing hydrogen ion or other analyte and either generates color or changes color. Depending on the selection of responsive material, the change is usually qualitative or, at best, semiquantitative. In certain fields, it is often required that analytical techniques yield rapid, quantitative results. Much recent development work has attempted to provide elements useful in diagnostic chemical analysis, where testing of biological liquids including body fluids such as blood, plasma, urine and the like, must produce highly quantitative results, rapidly and conveniently.

Solution chemical techniques have enjoyed broad acceptance in the clinical laboratory environment, particularly in automated analysis. Such techniques, however, require analyzer equipment having intricate solution handling and transport capabilities. Analytical equipment of the "wet chemistry" variety, illustrated for example in U.S. Pat. No. 2,797,149, U.S. Pat. No. 3,036,893 and U.S. Pat. No. 3,526,480 is often expensive and cumbersome, and further requires skilled personnel, both for operation and the precise cleaning needed to avoid sample to sample contamination.

As an alternative to solution chemistry, various integral elements for non-solution chemical analysis have been proposed. Although essentially dry analysis offers substantial storage, handling and other conveniences as compared to wet chemistry, variations of the "dry" approach have enjoyed only limited success and have been used primarily for qualitative and semi-quantitative test purposes.

2. Description of Related Art

A basic variety of integral and analytical element is described in U.S. Pat. No. 3,092,465. Such multi-layer elements use an absorbent carrier impregnated with one or more reagents, typically including a color former, over which is coated a semipermeable membrane. Upon contact with a test liquid, analyte passes through the membrane which prevents passage and absorption of certain interfering components that could impair the test results. Such elements do not yield highly quantitative results. For such reasons they have not been popular in certain test situations, as in clinical laboratory applications.

Integral analytical elements adapted for automated test procedures have also been described, such as in U.S. Pat. Nos. 3,368,872 and 3,526,480. Such descriptions refer to means for avoiding chromatographic effects (often called ringing, targeting or doughnuting) in the element by immobilizing reagent or including a means to decrease the tendency of an applied sample to exert a washing effect on incorporated reagent, as by use of simple porous members over a reagent carrying material. However, there is no suggestion of an efficient means to provide a uniform concentration of analyte to all reagent areas contacted by an applied sample, and such balanced concentration is extremely important if test results are to be interpretable by automated readout, whether densitometric, colorimetric, fluorometric, or otherwise.

The only disclosed means to provide a somewhat uniform concentration of analyte to an element's reagent areas has been by a technique that can be termed sample confinement. Usually, as is described in U.S. Pat. No. 3,368,872, a barrier is included on the element to confine an applied sample in a predetermined region of the element's surface, with the result that excess liquid is usually present on the element after sample application. This can create inconvenience in handling and cleanup and, more seriously, can require precise sample volume delivery when applying sample to the element.

There has been some recognition of the need to promote or avoid, as desired, the migration of reagents and sample constituents between layers of integral analytical elements, as is discussed in U.S. Pat. Nos. 2,761,813; 2,672,431; 2,672,432; 2,677,647; 2,923,669; 3,814,670 and 3,843,452. However, this has been in the context of elements for microbiological analysis. Such elements either do not indicate any means to effect or preserve concentrational uniformity, for example laterally within a layer, as by isotropic porosity or uniform permeability, or they require blended layers the interface of which is characterized by mutual penetration of the adjacent layers.

There is no suggestion in the related art that sample constituents should be encouraged to distribute within one layer to achieve therein concentrational unifomity for analyte or other substances that can be provided, still in uniform concentration, to an associated layer for analytical reactions or similar activity. In fact, the structural and chemical characteristics of materials used in the microbiological element (such as absorbent papers, wood, etc.) might impair such a result for reasons of physical restraint, non-uniform permeability or undesirable chemical binding. Additionally, the choice of fibrous absorbent materials could further frustrate highly accurate measurement, due to their nonuniform structure and texture.

As can be appreciated, obstacles to the more widespread use of elements for essentially dry analysis have included the inability of previous elements to produce highly quantitative, uniform test results and their lack of compatibility with machine handling and the automated readout and processing of test results. Improved elements are needed, particularly those able to perform the various sample handling and reaction functions apparently necessary to overcome problems such as those mentioned previously herein.

SUMMARY OF THE INVENTION

The present invention provides novel integral elements for analysis of liquids, such as biological liquids. As used herein, the term integral element refers to elements having at least two superposed layers, desirably discrete, in intimate contact. Preferably, such elements are formed prior to application of a liquid sample for analysis. Elements of this invention are capable of performing internally a variety of sample handling functions. They do not require expertise in their use and they can produce quantitative analytical results without the specialized spotting or other procedures such as sample confinement, washing or removal of excess sample, typically needed for analyses made using known elements. Further, the results produced by elements of this invention are substantially consistent and free from internal variations so that automated means of measuring electromagnetic radiation (radiometric techniques) can be used to detect such results, if necessary or desirable, with minimal risk of inconsistency.

Stated more particularly, the present invention provides integral analytical elements composed of multiple, superposed layers which can provide quickly within the element a highly quantitative, detectable change in response to the presence of an analyte in liquid applied to the element. Elements of this invention can be used for diagnostic purposes and include a sample spreading layer in fluid contact with a reagent layer. The sample spreading layer, synonymously referred to herein as a spreading layer or a metering layer, is capable of distributing or metering within the layer substance(s) including at least a component of a liquid sample applied to the element or a reaction product of such a component to provide, at any given time, a uniform concentration of such substance at the surface of the spreading layer facing, i.e. closer to, the reagent layer. The applied sample need not be confined. As will be appreciated, such concentration, although instantaneously uniform, can change over a period of time without deleterious effects. In various perferred embodiments, the spreading layer is isotropically porous; that is, it is porous in every direction within the layer. Reference herein to isotropic porosity identifies the fact of substantial porosity in all directions within the spreading layer. It will be understood that the degree of such porosity may be variable, if necessary or desirable, for example regarding pore size, percentage of void volume or otherwise. It shall be understood that the term isotropic porosity (or isotropically porous) as used herein should not be confused with the terms isoporous or ionotropic, often used with reference to filter membranes to signify those membranes having pores that are continuous between membrane surfaces. Likewise, isotropic porosity should not be confused with the term isotropic, used in contradistinction to the term anisotropic, which signifies filter membranes having a thin "skin" along at least one surface of the membrane. See for example, *Membrane Science and Technology*, James Flinn ed, Plenum Press, New York (1970).

The reagent layer is a layer containing at least one material that is interactive with an analyte or a precursor of a reaction product of an analyte, and within which a change can be produced by virtue of such interactive material. The reagent layer is preferably of substantially uniform permeability to at least one substance spreadable within the spreading layer or a reaction product of such a substance. Uniform permeability of a layer refers to permeability such that, when a homogeneous fluid is provided uniformly to a surface of the layer, identical measurements of the concentration of such fluid within the layer, but made through different regions of a surface of the layer, will yield substantially equal results. By virtue of uniform permeability, undesirable concentration gradients within, for example, a reagent layer as described herein, are avoided.

Reference herein to fluid contact between a spreading layer and a reagent layer in an integral analytical element identifies the ability of a fluid, whether liquid or gaseous, to pass in such element between superposed regions of the spreading layer and the reagent layer. Stated in another manner, fluid contact refers to the ability to transport components of a fluid between the layers in fluid contact. In the case of analysis for nitrogen containing compounds, ammonia or other nitrogen containing gaseous materials may comprise fluid passing between spreading layer and reagent layer. Although such layers in fluid contact can be contiguous, they may also be separated by intervening layers. However, layers in the element that physically intervene a spreading layer and reagent layer in mutual fluid contact will also be in fluid contact and will not prevent the passage of fluid between the fluid contacting spreading and reagent layers.

The elements of this invention can be self-supporting or the spreading layer, reagent layer in fluid contact with the spreading layer and any other layers can be carried on a support, such as a support that can transmit electromagnetic radiation of one or more wavelengths within the region between about 200 nm and about 900 nm.

An exemplary analytical element of this invention can receive a liquid sample which is distributed, as discussed elsewhere herein, within the metering layer such that, at any given time, a uniform concentration of substance including at least a component of the sample or a reaction product of such component is provided at the surface of the metering layer facing the reagent layer. It is possible to obtain such uniform concentration over a wide range of sample volumes applied to the element. Due to fluid contact between the metering layer and the reagent layer and also to the uniform permeability of the reagent layer to substance spread within the spreading layer or to reaction products of such substance, uniformly metered constituents are provided from the spreading layer to the reagent layer and can penetrate the reagent layer essentially without the occurrence therein, at any instant in time, of significant variations in the concentration of such substance or reaction product inconsistent with those obtained as a result of uniform permeability. Due to the presence of an interactive (e.g. chemically reactive) material, and a uniform apparent concentration of substance provided from the metering layer to the reagent layer, a uniform, quantitative detectable change can be produced in the element. Such a change, which can be the generation or destruction of coloration or fluorescence, can be detected quantitatively by radiometric techniques and, if desired, by automatic radiometric sensing devices such as photometric devices. As is explained elsewhere herein, other layers, such as filter layers, registration layers, and/or reflective layers can be used in association with the spreading and reagent layers.

BRIEF DESCRIPTION OF THE DRAWINGS

In the accompanying drawings, each of FIG. 1, FIG. 2, FIG. 3.

DESCRIPTION OF PREFERRED EMBODIMENTS

Figure 1:
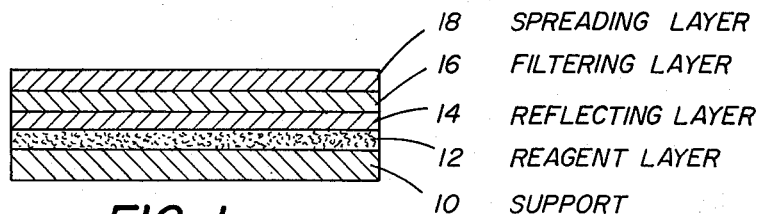

The integral elements of this invention include a spreading layer in fluid contact with a reagent layer, wherein the spreading layer is capable of spreading within itself substance including at least a component of a liquid sample or a reaction product of such component to provide a uniform concentration of such spread substance at the surface of the spreading layer facing the reagent layer and wherein the reagent layer is of substantially uniform permeability to at least a constituent of substance spreadable in the spreading layer or a reaction product of such constituent. The spread substance may be a component of a liquid sample applied to the element, for example when the analyte is usually present in the liquid under analysis, as in the case of glucose in whole blood or serum. The spread substance may also be a reaction product of such a component, for example, when proteins or other higher molecular weight materials are broken down for further analysis essentially on contact with the element.

In one aspect, the integral elements of this invention can include an isotropically porous spreading layer in fluid contact with a reagent layer of substantially uniform permeability to at least substance spreadable within the spreading layer or a reaction product of such a substance.

As used herein, the term spreading layer defines a layer, isotropically porous or otherwise, that can accept a liquid sample, whether applied directly to the spreading layer or provided to it from a layer or layers in fluid contact with the spreading layer, and within which the solvent or dispersion medium of the sample and at least one solute, dispersoid (constituent of the dispersed or internal phase) or reaction product of solute or dispersoid is distributed such that a uniform concentration of such substance, i.e. solute, dispersoid or reaction product thereof, is provided at the surface of the spreading layer facing the reagent layer(s) of the element. It will be appreciated that such a concentration can be achieved with concentration gradients present through the thickness of or otherwise in the spreading layer. Such gradients do not present any difficulty to obtaining quantitative test results and can be accommodated using known calibration techniques.

The mechanism of spreading is not fully understood, but it is theorized that spreading results from and is limited by a combination of forces such as hydrostatic pressure of a liquid sample, capillary action within the spreading layer, surface tension of the sample, wicking action of layers in fluid contact with the spreading layer, and the like. As will be appreciated, the extent of spreading is dependent in part on the volume of liquid to be spread. However, it should be emphasized that the uniform concentration obtained with spreading is substantially independent of liquid sample volume and will occur with varying degrees of spreading. As a result, elements of this invention do not require precise sample application techniques. However, a particular liquid sample volume may be desirable for reasons of preferred spread times or the like. Because the elements of this invention are able to produce quantitative results using very small sample volumes that can be entirely taken up within a conveniently sized region of the spreading layer (e.g. one square centimeter), there is no need to remove excess moisture from the element after application of a liquid sample. Further, because spreading occurs in the spreading layer and the spread substance is provided to the fluid contacting reagent layer and without apparent substantial lateral hydrostatic pressure, there is not the "ringing" problem often seen with prior analytical elements when soluble reagents were used.

The spreading layer need only produce a uniform concentration of spread substance per unit area at its surface facing a reagent layer with which the spreading layer is in fluid contact, and it is very convenient to determine whether a particular layer can be suitable for spreading purposes. Such uniformity of concentration can be determined by densitometric or other analytical techniques, as by scanning the appropriate surface or reagent layer or other associated layer to determine the apparent concentration of spread substance or of any reaction product based on the concentration of spread substance. The following test is intended only as an example and the selection of materials or test parameters does not indicate, expressly or by implication, that other materials or parameters may not be suitable for similar purposes.

In conducting such a test one can apply to a transparent photograph film support material, such as subbed poly (ethylene terephthalate), a transparent gelatin layer at a gelatin coverage of about 200 mg/dm$^2$. The gelatin may vary in hardness, but for testing purposes a layer of gelatin hardened to swell the layer thickness by about 300 percent when immersed for 5 minutes in 22° C water is suitable. When dry, the gelatin layer will have a thickness of about 30 microns. Over the gelatin layer can be applied, such as as by coating from solution or dispersion, the layer to be evaluated for spreading purposes. Spreading layers can be designed to have widely varying dry thicknesses, and a thickness of from about 100 to about 200 microns, is convenient for test purposes. After drying the layers, a sample of test solution or dispersion can be applied to the surface of the spreading layer under evaluation, preferably in a small quantity so that not all portions of the layer are wetted by the applied sample, but desirably sufficient to create a wetted region that can include a circular area of about 8–10 millimeters in diameter. The selection of a test solution or dispersion is a matter of choice and will depend in part on the type of sample or analyte to which the layer will be exposed under conditions of actual usage. For low molecular weight materials, aqueous dye solutions can be used and a 0.0005 weight percent solution of Solatine Pink is acceptable. For higher molecular weight materials such as proteins, an aqueous dispersion of bovine albumin dyed with Solatine Pink can be used. After applying the liquid sample to the layer under evaluation and allowing the liquid sample to disappear from the surface of and be taken up into the layer, the test element can be turned over and the bottom surface of the proposed spreading layer can be viewed through the transparent support material and gelatin layer. If, prior to substantial evaporation of solvent or dispersion medium, the colored spot is of a substantially uniform color density when scanned by a densitometer having a circular aperture of about 2–3 millimeters, then spreading and the achievement of a uniform apparent concentration at the bottom surface of the test layer and/or in the gelatin layer has taken place and the test layer may be useful as a spreading layer in analytical elements of the type described herein. By substantially uniform density is meant a density across the spot, with the exception of its periphery, having maximum and minimum values not more than ±10–15 percent from the mean density. Due to edge effects, non-characteristic density gradients may arise at the spot periphery but need have no effect on the significance of an analytical result. Peripheral area can vary between spots, but it will usually not be more than about 20 percent of the entire spot and may be less.

As mentioned herein, useful spreading or metering layers can be isotropically porous layers. Such layers can be prepared using a variety of components. In one aspect, particulate material can be used to form such layers, wherein the isotropic porosity is created by interconnected spaces between the particles. Various types of particulate matter, all desirably chemically inert to sample components under analysis, are useful. Pigments, such as titanium dioxide, barium sulfate, zinc oxide, lead oxide, etc., are desirable. Other desirable particles are diatomaceous earth and microcrystalline colloidal materials derived from natural or synthetic polymers. Such microcrystalline materials are described in an article entitled, "Colloidal Macromolecular Phenomena, Part II, Novel Microcrystals of Polymers" by O. A. Battista et al. published in the Journal of Applied Polymer Science, Vol. 11, pages 481–498 (1967). Microcrystalline cellulose, which is commercially available from FMC Corporation under the name Avicel, is an example of such a colloidal material which is satisfactory for use in the present invention. Spherical particles of uniform size or sizes, such as resinous or glass beads, can also be used and may be particularly desirable where uniform pores are advantageous, such as for selective filtration purposes. If a particulate material of choice is not adherent, as in the case of glass beads or the like, it can be treated to obtain particles that can adhere to each other at points of contact and thereby facilitate formation of an isotropically porous layer. As an example of suitable treatment, non adherent particles can be coated with a thin adherent layer, such as a solution of hydrophilic colloid like gelatin or polyvinyl alcohol, and brought into mutual contact in a layer. When the colloid coating dries, the layer integrity is maintained and open spaces remain between its component particles.

As an alternative or in addition to such particulate materials, the spreading layer can be prepared using isotropically porous polymers. It is possible to prepare such polymers using techniques useful in forming "blush" polymers. Blush polymer layers can be formed on a substrate by dissolving a polymer in a mixture of two liquids, one of which is a lower boiling, good solvent for the polymer and the other of which is of a higher boiling point and is a non-solvent or at least a poor solvent for the polymer. Such a polymer solution is then coated on the substrate, and dried under controlled conditions. The lower boiling solvent evaporates more readily and the coating can become enriched in the liquid which is a poor solvent or non-solvent. As evaporation proceeds, under proper conditions, the polymer forms as an isotropically porous layer. Many different polymers can be used, singly or in combination, for preparing isotropically porous blush polymer spreading layers for use in this invention, typical examples being polycarbonates, polyamides, polyurethanes and cellulose esters such as cellulose acetate.

Reagent layers in the elements of this invention are desirably uniformly permeable, and optionally porous if appropriate, to substance spreadable within the metering or spreading layer and to reaction products of such substance. As used herein the term permeability includes permeability arising from porosity, ability to swell or any other characteristic. Such layers can include a matrix in which is distributed, i.e. dissolved or dispersed, a material that is interactive with an analyte or a precursor to or a reaction product of an analyte. The choice of a matrix material is, of course, variable and dependent on the intended use of the element. Desirable matrix materials can include hydrophilic materials including both naturally occurring substances like gelatin, gelatin derivatives, hydrophilic cellulose derivatives, polysaccharides such as dextran, gum arabic, agarose and the like, and also synthetic substances such as water-soluble polyvinyl compounds like poly (vinyl alcohol) and poly (vinyl pyrrolidone), acrylamide polymers, etc. Organophilic materials such as cellulose esters and the like can also be useful, and the choice of materials in any instance will reflect the use for which a particular element is intended. To enhance permeability of the reagent layer, if not porous, it is often useful to use a matrix material that is moderately swellable in the solvent or dispersion medium of liquid under analysis. The choice of a reagent layer matrix, in any given instance, may also depend in part on optical properties of the resultant layers, if photometric (including fluorometric) sensing of an analytical result is intended. Also, it may be necessary to select a material that is compatible with the application of adjacent layers during manufacture of the element. As an example, where the formation of discrete layers is desired and the intended analysis will be of aqueous liquids, it may be appropriate to select an essentially water soluble matrix for the reagent layer and essentially organosoluble or organo dispersible ingredients for an adjacent layer, such as a spreading layer. In such manner, mutual solvent action is minimized and a clearly delineated layer structure can be formed. In many cases, to facilitate the formation within the spreading layer of such concentrational uniformity as is discussed herein, it may be desirable to have the reagent layer of lower permeability than is the spreading layer itself. Relative permeability can be determined by well-known techniques.

Within the reagent layer is distributed a material that can interact with an analyte or a precursor or reaction product of an analyte. Such interaction is meant to refer to chemical reactivity, catalytic activity as in the formation of an enzyme-substrate complex, and any other form of chemical or physical interaction that can produce or promote within the element, such as in the reagent layer, a change that is radiometrically detectable, that is, by suitable measurement of light or other energy. The distribution of interactive material can be obtained by dissolving or dispersing it in the matrix material. Although uniform distributions are often preferred, they may not be necessary if the interactive material is, for example, an enzyme. Reagents or other interactive materials soluble in the liquid under analysis may advantageously be immobilized in the reagent layer, particularly when the reagent layer is porous. The particular interactive materials that may be distributed within a reagent layer will depend on the analysis of choice. In the case of glucose analysis, a ferricyanide compound can be used. Glucose reacts with ferricyanide and the reaction causes a decrease in the yellow color characteristic of ferricyanide. In testing for uric acid, as in blood or serum, a mixture of copper sulfate and neocuproine can be distributed in the reagent layer matrix. Uric acid causes reduction of cupric copper to cuprous copper that can complex with the neocuproine to form a colored material that is proportional in density to the concentration of uric acid in the analyzed liquid. In the case of many analyses, enzymes such as oxidase materials like glucose oxidase or cholesterol oxidase may desirably be included as interactive materials within the reagent layer. If an element is prepared according to the present invention, but without an interactive material in the "reagent" layer, it could be useful for direct analysis of analyte materials spreadable within the spreading layer.

In preparing integral analytical elements of this invention, the layers can be preformed separately and laminated to form the overall element. Layers prepared in such a manner are typically coated from solution or dispersion on a surface from which the dried layer can be physically stripped. However, a convenient method which can avoid problems of multiple stripping and lamination steps is to coat an initial layer on a stripping surface or a support, as desired, and thereafter to coat successive layers directly on those coated previously. Such coating can be accomplished by hand, using a blade coating device or by machine, using techniques such as dip or bead coating. If machine coating techniques are used, it is often possible to coat adjacent layers simultaneously, using hopper coating techniques well known in the preparation of light-sensitive photographic films and papers. If it is essential or desirable that adjacent layers be discrete, and maintenance of layer separation by adjustment of coating formulation specific gravity is not satisfactory, as possibly in the case of porous spreading layers, the appropriate selection of components for each layer, including solvent or dispersion medium, can minimize or eliminate interlayer component migration and solvent effects, thereby promoting the formation of well-defined, discrete layers. Any interlayer adhesion problems can be overcome without harmful effect by means of surface treatments including extremely thin application of subbing materials such as are used in photographic films.

For reagent layers, a coating solution or dispersion including the matrix and incorporated interactive materials can be prepared, coated as discussed herein and dried to form a dimensionally stable layer. The thickness of any reagent layer and its degree of permeability are widely variable and depend on actual usage. Dry thicknesses of from about 10 microns to about 100 microns have been convenient, although more widely varying thicknesses may be preferable in certain circumstances. For example, if comparatively large amounts of interactive material, e.g. polymeric materials like enzymes, are required, it may be desirable to use slightly thicker reagent layers.

In addition to its uniform permeability, the reagent layer is desirably substantially free from any characteristic that might appear as or contribute to mottle or other noise in the detection of an analytical result produced in an integral element of the invention. For example, any variations in color or in texture within the reagent layer, as could occur if certain fibrous materials, e.g. some papers, are used as a permeable medium, may be disadvantageous due to non-uniform reflectance or transmittance of detecting energy. Further, although fibrous materials like filter and other papers are generally permeable overall, some such materials typically can exhibit widely ranging degrees of permeability and may not exhibit uniform permeability, for example, based on structural variations such as fiber dimensions and spacing. As a result, such materials not uniformly permeable are not preferred in reagent layers of the present invention. Spreading layers and reagent layers of the present elements include non-fibrous materials, consistent with appropriate sample spreading and result detection within such layers, as discussed elsewhere herein.

Spreading layers can also be prepared by coating from solution or dispersion. As stated previously, spreading and associated layers of an element are in a superposed relationship such that a spreading layer is in fluid contact with a reagent layer. The range of materials useful for inclusion in any spreading layer is widely variable as discussed herein and will usually include predominantly materials that are resistant to, i.e. substantially non-swellable upon contact with, the liquid under analysis. Swelling of about 10–40 percent of the layer's dry thickness may be normal. The thickness of the spreading layer is variable and will depend in part on the intended sample volume, which for convenience and cleanliness the spreading layer should be able to absorb, and on the layer's void volume, which also affects the amount of sample that can be absorbed into the layer. Spreading layers of from about 50 microns to about 300 microns have been particularly useful. However, wider variations in thickness are acceptable and may be desirable for particular elements.

When preparing an isotropically porous spreading layer, it is useful to have void volume comprise at least about 25 percent of the total layer volume, and void volumes of from 50–95 percent may be desirable. Variations in void volume of porous spreading layers can be used advantageously to modify element characteristics such as total permeability of the spreading layer or the time needed for sample spreading to occur. As can be appreciated, void volume within the layer can be controlled, for example, by selecting particulate materials of appropriate size, or by varying the solvents or drying conditions when isotropically porous blush polymers are used in the spreading layer. The void volume of any such layer can be calculated with reasonable accuracy by a variety of techniques such as the statistical method described in Chalkley, *Journal of the National Cancer Institute*, 4, 47 (1943) and by direct weighing and determining the ratio of actual weight of the layer to the weight of solid material equal in volume to that of the layer, comparably composed of constituents from the layer. It will be appreciated that the pore size in any case should be sufficient to permit spreading of initial sample components or other substances desirably provided to a reagent layer.

As mentioned previously herein, the integral analytical elements can be self-supporting or coated on a support. Useful support materials include paper and polyolefin coated paper, as well as a variety of polymeric materials such as cellulose acetate, poly(ethylene terephthalate), polycarbonates and polyvinyl compounds such as polystyrenes, etc. The support can be opaque or it can transmit light or other energy. A support of choice for any particular element will be compatible with the intended mode of result detection. Preferred supports include transparent support materials capable of transmitting electromagnetic radiation of a wavelength within the region between about 200 nm and about 900 nm. The support need not, of course, transmit over the entire 200–900 nm region, although for fluorometric detection of analytical results through the support, it is desirable for the support to transmit over a wider band or, alternatively, to transmit at the absorption and emission spectra of the fluorescent materials used for detection. It may also be desirable to have a support that transmits one or more narrow wavelength bands and is opaque to adjacent wavelength bands. This could be accomplished, for example, by impregnating or coating the support with one or more colorants having suitable absorption characteristics. When an element includes a support, a reagent layer will usually be interposed in the element between the support and a spreading layer, which often is the outermost layer in an element.

The components of any particular layer of an integral analytical element of this invention, and the layer configuration of choice, will depend on the use for which an element is intended. As stated previously, spreading layer pore size can be chosen so that the layer can filter out undesirable sample components that would, for example, interfere with an analytical reaction or with the detection of any test result produced within the element. For analysis of whole blood, porous layers having a pore size of from 1 to about 5 microns are particularly useful in screening out blood cells, which typically have a size of from about 7 to about 30 microns. If desirable, an element can include a plurality of spreading layers, each of which may be different in its ability to spread and filter. Also, if a restraint on transport of substances within the element additional to that provided by spreading layers is needed, a filter or dialysis layer can be included at an appropriate location in the element. As an example, in analyzing for blood glucose, a dialysis layer such as a semipermeable cellulose memebrane can prevent passage of proteins or other potentially interfering substances to the reagent layer.

It can also be desirable to include within an element one or more reflective layers, optionally absorptive to detecting radiation, such as to facilitate result detection by reflection radiometry, e.g. reflection photometry or a similar technique. Such reflectance can be provided by a layer also serving, for example, as a spreading layer or it can be provided by an additional layer that may not have an additional function within the element. Pigments, such as titanium dioxide and barium sulfate, are reflective and can be used to advantage in a reflecting layer. Blush polymers can also constitute a suitable reflecting material. As can be appreciated, pigment spreading layers may be useful for this purpose as can blush polymer layers that may also be spreading layers. In one preferred aspect, blush polymer layers can also incorporate a pigment to enhance spreading and/or reflectivity. The amount of pigment that can be included in a layer together with blush polymer is highly variable, and amounts of from about 1 to about 10 parts by weight of pigment per part by weight of blush polymer are preferred, with from about 3 to about 6 parts pigment per part of blush polymer being most preferred.

In the layers of the element, it can be advantageous to incorporate one or more surfactant materials such as anionic and nonionic surfactant materials. They can, for example, enhance coatability of layer formulations and enhance the extent and rate of spreading in spreading layers that are not easily wetted by liquid samples in the absence of an aid such as a surfactant. Interactive materials can also be present in the spreading layer if desirable for a particular analysis. As an example, proteins or other higher molecular weight materials can, for convenience, be divided into more easily spreadable, lower molecular weight components that may also be more suitable for an analytical reaction, such as by having in the spreading layer an appropriate interactive material such as an enzyme, e.g. a protease or esterase. In layers of the element it can also be desirable to include materials that can render non-active in the analysis of choice by chemical reaction or otherwise, materials potentially deleterious to such analysis. As an example, ascorbate oxidase may be incorporated in an element to remove ascorbate ion which may interfere with analysis for glucose.

In still another aspect, an analysis of choice may require a multi-stage reaction that can best be accomplished in an element having a plurality of reagent layers, each of which may be adapted to enhance or effect particular reaction stages. As an example, in the determination of the enzyme known as serum glutamic-oxalacetic transaminase, sequential reactions can be used. This enzyme catalyzes the conversion at a pH of 7.4 of $\alpha$-ketoglutarate and aspartate ions to the corresponding oxalacetate and glutamate. The oxalacetate can be measured by its reaction with NADH catalyzed by maleic dihydrogenase wherein the oxalacetate is converted to the corresponding malate and the NADH is oxidized to NAD+. The course of the reaction is observed by noting decrease in fluorescence or absorption of NADH. To facilitate the desired reactions, the reagents can be separated into two layers, preferably discrete. Thus, the $\alpha$-ketoglutarate and asparate can be incorporated in a first reagent layer which is coated over a second reagent layer that contains the maleic dehydrogenase and NADH.

To facilitate the detection of any change produced in an element as described herein, such as change in coloration, optical density or fluorescence, it can be desirable for the element to include a layer to receive any reaction products or other materials, the relative presence or absence of which relates to detection of an analytical result. Such a layer, conveniently referred to as a registration layer, is desirably in fluid contact with a reagent layer and may be separated from such reagent layer by a reflecting and/or opaque layer to facilitate the result detection by various radiometric techniques. Such registration layers can include hydrophilic colloids, such as those useful in reagent layers. Additionally, where dyestuffs are produced in the element, the registration layer may contain mordant materials such as those useful in color photographic films and papers. Additionally, the registration layer can also contain, if desirable, interactive materials such as leuco dyes or other materials appropriate to form initially in the registration layer materials that contribute to the detection of an analytical result.

Integral analytical elements of the present invention can be adapted for use in carrying out a wide variety of chemical analyses, not only in the field of clinical chemistry but in chemical research and in chemical process control laboratories. They are well suited for use in clinical testing of body fluids, such as blood, blood serum and urine, since in this work a large number of repetitive tests are frequently conducted and test results are often needed a very short time after the sample is taken. In the field of blood analysis, for example, the multilayer element can be adapted for use in carrying out quantitative analyses for many of the blood components which are routinely measured.

Thus, for example, the element may be readily adapted for use in the analysis of such blood components as albumin, bilirubin, urea nitrogen, serum glutamic-oxalacetic transaminase, chloride, glucose, uric acid, and alkaline phosphatase, as well as many other components, by appropriate choice of test reagents or other interactive materials. In analyzing blood with an analytical element of this invention, the blood cells may first be separated from the serum, by such means as centrifuging, and the serum applied to the element. However, it is not necessary to make such separation, especially if reflective spectrophotometric analysis techniques are used to quantify or otherwise analyze the reaction product formed in the element as whole blood can be applied directly to the element and the blood cells filtered out through the action of a filtering layer. The presence of these cells on the element will not interfere with spectrophotometric analysis if it is carried out by reflection techniques, with light being transmitted through the support and reagent layer and reflected from the porous reflecting layer or other layer such that detecting radiation does not intercept the cells. A particularly significant advantage of the integral analytical elements described herein is their ability to be used to analyze either serum or whole blood.

As can be appreciated, a variety of different elements, depending on the analysis of choice, can be prepared in accordance with the present invention. Elements can be configured in a variety of forms, including elongated tapes of any desired width, sheets or smaller chips. Particular elements can be adapted for one or more tests of a single type or a variety of tests of differing types. In such latter event, it can be desirable to coat a common support with one or more strips or channels, each optionally of a different composition to form a composite element suited for conducting a variety of desired tests.

Figure 2:
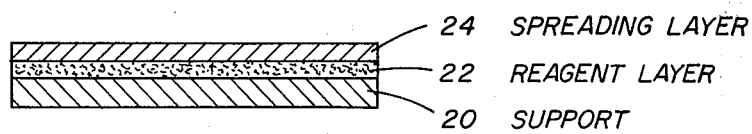
Figure 3:
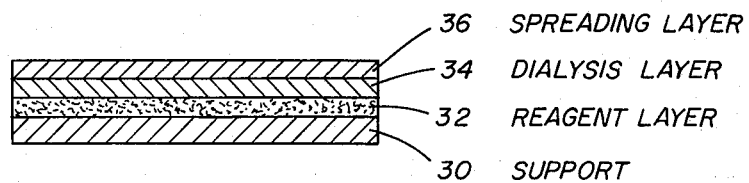
Figure 4:
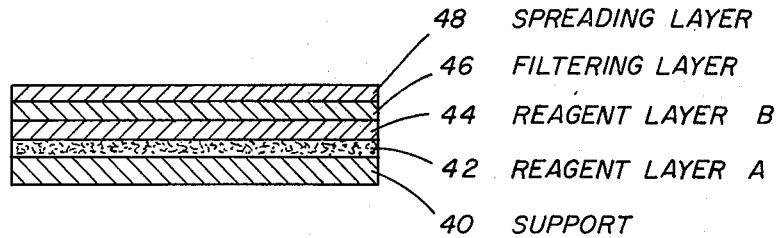
FIG. 4 is an enlarged sectional view of a preferred embodiment illustrating an integral analytical element of this invention.

Exemplary elements of this invention include those illustrated in the accompanying drawings. In FIG. 1 is represented an analytical element composed of a support 10, on which is coated a reagent layer 12, a reflecting layer 14 which provides a white background for analytical result detection, such as by reflection spectrophotometry, a filtering layer 16, and a sample spreading layer 18. Detection can be done through the support, if suitably transmissive at the detecting wavelength. Reagent layer 12 can be composed of a solution or dispersion of one or more test reagents in a binder such as gelatin, while each of layers 14, 16 and 18 can be a blush polymer having isotropic porosity and/or pore size as may be needed for the particular function each layer is intended to perform. The spreading layer 18 and the reagent layer 12 will be in fluid contact. In an alternative embodiment of the invention shown in FIG. 2, the analytical element is composed of a support 20 bearing a reagent layer 22 in fluid contact with a spreading layer 24 which can also serve the function of filtering and also may provide a suitably reflective background for reflection spectrophotometric detection through support 20. Alternatively, layer 24 may be such that it does not reflect and detection can be accomplished in the transmission mode. Layer 24 can be, for example, an isotropically porous blush polymer layer which has been coated or laminated over layer 22. FIG. 3 illustrates a further embodiment of the invention in which the analytical elememt is composed of support 30, reagent layer 32, a dialysis layer 34 which can be formed from a semi-permeable membrane and a spreading layer 36, such as an isotropically porous blush polymer layer, which can serve the functions of spreading and filtering and which can provide a suitable background for reflection spectrophotometry through support 30. The spreading layer and reagent layer are in fluid contact. A still further embodiment of the invention is shown in FIG. 4 in which the analytical element is composed of support 40, a reagent layer (A) 42, a second reagent layer (B) 44, a layer 46 which serves as a filtering and light reflecting layer, and a spreading layer 48 which is in fluid contact with both reagent layers. Layer 46 can be composed, for example, of titanium dioxide in blushed cellulose acetate and layer 48 can be composed of diatomaceous earth in blushed cellulose acetate or of glass beads mutually adhered with a hydrophilic colloid like gelatin.

The present elements are placed in use by applying to the element a sample of liquid under analysis. Typically, an element will be formed such that an applied sample will contact a spreading layer prior to a nonspreading reagent layer and will first contact such spreading layer at its surface farther from such reagent layer. Because analytical accuracy of the present elements is not substantially diminished by variations in the volume of applied samples, due to the novel relationship of spreading layer and fluid contacting reagent layer, sample application by hand or machine is acceptable. For reasons of convenience in detecting an analytical result, however, reasonable consistency in sample volume may be desirable. As discussed previously, the spreading layer is also extremely desirable in minimizing the occurrence of ringing when soluble interactive materials are used in a reagent layer.

In a typical analytical procedure using the present elements, which could be manual or automated, the element is taken from a supply roll, chip packet or other source and positioned to receive a free drop, contact spot or other form of liquid sample, such as from an appropriate dispenser. After sample application, and desirably after the liquid sample has been taken up by the spreading layer, the element is exposed to any conditioning, such as heating, humidification or the like, that may be desirable to quicken or otherwise facilitate obtaining any test result. If an automated procedure is used, it can also be desirable to have the spreading layer accomplish its function within several seconds. This can be accomplished conveniently by appropriate selection of various parameters, such as layer thickness, void volume in porous layers, etc.

After the analytical result is obtained as a detectable change, it is measured, usually by passing the element through a zone in which suitable apparatus for reflection, transmission or fluorescence spectrophotometry is provided. Such apparatus would serve to direct a beam of energy, such as light, through the support which is then reflected from the element back to a detecting means or passes through the element to a detector in the case of transmission detection. In a preferred mode, the analytical result is detected in a region of the element totally within the region in which such result is produced. Use of reflection spectrophotometry can be advantageous in some situations as it effectively avoids optical interference from any residues, such as blood cells, which have been left on or in the layers of the element. Conventional techniques of fluorescence spectrophotometry can also be employed if desired. Furthermore, when blood serum is tested or means are provided for eliminating unwanted whole blood residues, transmission techniques can be used to detect and quantify the indicating reaction products by directing a flow of radiant energy, for example, U.V. visible or I.R. radiation at one surface of the element and measuring the output of that energy from the opposing surface of the element. Generally, electromagnetic radiation in the range of from about 200 to about 900 nm has been found useful for such measurements, although any radiation to which the element is permeable and which is capable of quantifying the product produced in the reagent layer can be used. Various calibration techniques can be used to provide a control for the analysis as one example, a sample of analyte standard solution can be applied adjacent to the area where the drop of sample is placed in order to permit the use of differential measurements in the analysis.

The following examples of integral analytical elements are provided to further illustrate the present invention.

EXAMPLE 1

Each of three analytical elements was prepared as follows: A reagent layer consisting of glucose oxidase at 3.15 mg/dm$^2$, peroxidase at 3.95 mg/dm$^2$, o-dianisidine hydrochloride at 4.42 mb/dm$^2$ and gelatin at 215 mg/dm$^2$ was coated on a 4-mil thick poly(ethylene terephthalate) support and dried. A slurry was then prepared by mixing 12.0 grams of TiO$_2$ and 50 milliliters of a 3% by weight solution of cellulose acetate in acetone and diluting to a volume of 80 millimeters with a mixture of equal parts by volume of acetone and xylene. The slurry was coated over the reagent layer at a coverage of 300 mg/dm$^2$ of TiO$_2$ and 37.2 mg/dm$^2$ of cellulose acetate and dried to form a pigment/blush polymer layer adapted to serve as both a filtering and light reflecting layer. A spreading layer was then coated over the filter/reflecting layer from a slurry of diatomaceous earth, salicyclic acid and cellulose acetate in a mixture by volume of 1.2 parts dichlorethane to one part acetone. Each of the three analytical elements included a different amount of diatomaceous earth in the spreading layer, and each was tested for its ability to effectively spread blood by depositing a 10 microliter sample of whole blood on its spreading layer. The time required for the applied liquid to diffuse completely into the spreading layer and the diameter of the spot formed on each element, as measured through the support, were determined for each of the three elements. Results obtained were as follows:

| Test Element No. | Diatomaceous Earth (mg/dm$^2$) | Salicyclic Acid (mg/dm$^2$) | Cellulose Acetate (mg/dm$^2$) | Diffusion Time (seconds) | Spot Diameter (centimeters) |
|---|---|---|---|---|---|
| 1 | 300 | 3.00 | 37.2 | 26 | 1.05 |
| 2 | 375 | 3.75 | 37.2 | 41 | 1.00 |
| 3 | 450 | 4.50 | 37.2 | 31 | 1.00 |

The analytical elements described in this example are useful for the detection of glucose in blood, with the presence of glucose being indicated by the formation of a medium brown color in the reagent layer. In each case, the filter layer prevented blood cells from reaching the reagent layer. The reagent layer, which was in fluid contact with the spreading layer, received fluid components of the samples and accordingly produced the colored spot.

EXAMPLE 2

A reagent layer consisting of a dispersion of copper sulfate and neocuproine in gelatin was coated on a 4-mil thick poly(ethylene terephthalate) film at a coating weight of 0.84 mg/dm$^2$ of copper sulfate, 1.28 mg/dm$^2$ of neocuproine and 53.9 mg/dm$^2$ of gelatin, and dried. To form a multilayer analytical element in accordance with the present invention, there was laminated to this reagent layer a microporous filter material having a thickness of 180 microns and an average pore size of 1.2 microns. The filter material employed was a commercially available cellulose acetate nitrate microporous membrane sold by Millipore Corporation under the trademark Millipore MF filter. It was laminated to the reagent layer by first steaming the reagent layer for several seconds to soften it, then pressing the spreading layer into contact with the reagent layer, and then rolling under light pressure to effect bonding. The layer of filter material was utilized to perform the function of filtering components such as blood cells from an applied sample and to provide a suitable background for result detection by reflection spectrophotometry. To form a spreading layer, spherical glass beads of 80 to 120 mesh in size, were mixed in a proportion of one gram of beads to 0.5 milliters of a solution containing 2.5% by weight gelatin and 0.01% by weight of a surface active agent sold by Olin Mathieson Company under the name Surfactant 10G (a para-isononylphenoxy polyglycidol ether having ten glycidol units). The resulting slurry was spread in a thin layer, such that the amount of slurry containing one gram of beads covered an area of 27 cm$^2$, over the layer of microporous filter material. A 10 microliter sample of whole blood was deposited on the sample spreading layer and spread in less than one second to a circular area of approximately one centimeter in diameter. The spreading layer was in fluid contact with the reagent layer, and pink coloration formed in the reagent layer.

EXAMPLE 3

A self-suppporting element for the analysis of glucose, such as in body fluids was prepared in the following manner. Coating coverages for each component is indicated in parentheses following identification of the component.

An unsubbed cellulose acetate film support was coated with an aqueous formulation: 1,7-dihydroxynaphthalene (0.64 g/m$^2$), 4-aminoantipyrine (0.86 g/m$^2$), glucose oxidase (29,000 U/m$^2$), peroxidase (10,020 U/m$^2$), glycerol (2.16 g/m$^2$) Surfactant 10G$^R$ (0.39 g/m$^2$), bis(vinylsulfonylmethyl)ether (0.26 g/m$^2$) and gelatin (21.7 g/m$^2$) and dried to prepare a reagent layer. The reagent layer was then overcoated with a subbing material poly(N-isopropylacrylamide) (0.3 g/m$^2$) followed by coating with the formulation cellulose acetate (6.6 g/m$^2$), titanium dioxide (46.0 g/m$^2$) and Estane 5711 (a polyurethane elastomer available from B. F. Goodrich, 1.38 g/m$^2$) which was coated from a mixture of acetone, dichloroethane and xylene and dried under controlled conditions to prepare an isotropically porous pigment/blush polymer reflecting/spreading layer.

After drying, the coated layers were stripped from the cellulose acetate film support to yield a self-supporting integral element which was cut into smaller elements that were mounted in cardboard holding frames. Several of the smaller elements were tested by applying to the elements 10 μ l samples of reconstituted serum containing 100, 200, 400, 600, 800 mg/dl of glucose. On each such element, a red spot formed in the reagent layer. After 20 minutes at room temperature (20° C) the reflection densities of the colored spots were measured using a Macbeth RD-514 reflection densitometer through a magenta filter. Results were as follows:

| Conc. of glucose | Magenta Density |
|---|---|
| 100 mg/dl | 0.55 |
| 200 mg/dl | 0.89 |
| 400 mg/dl | 1.44 |
| 600 mg/dl | 1.81 |
| 800 mg/dl | 2.02 |

It will be understood that the selection of interactive materials will depend on the test of choice. For example, when testing for chloride, such as in body fluids, silver chromate can be used which in the presence of chloride, effects a reddish brown to yellow color change in the element. In testing for albumin, hydroxyphenylbenzoic acid can be used and effect, when albumin is present in the element, the generation of a pinkish-orange color. In testing for glycerol, a combination of glycerol dehydrogenase, albumin, resazurin and diaphorase can be used. When glycerol is present in the element, fluorescense quantitative to the glycerol concentration is obtainable upon impingement of exciting radiation.

The invention has been described in detail with particular reference to certain preferred embodiments thereof but it will be understood that variations and modifications can be effected within the spirit and scope of the invention.

There is claimed:

1. An integral element for analysis of liquids, said element comprising, in fluid contact, an isotropically porous spreading layer comprising a non-fibrous material, and a reagent layer permeable to a substance spreadable within the spreading layer or a reaction product of such a substance.

2. An integral element as described in claim 1 and further comprising a plurality of isotropically porous spreading layers.

3. An integral element as described in claim 1, wherein the isotropically porous layer is an outer layer of said element.

4. An integral element as described in claim 1 and further comprising a plurality of reagent layers.

5. An integral element as described in claim 1, wherein the isotropically porous layer is resistant to liquid under analysis.

6. An integral element as described in claim 5 wherein the reagent layer is of lower permeability to the spreadable substance than is the spreading layer.

7. An integral element for analysis of liquids, said element comprising a support having thereon, in fluid contact, an isotropically porous spreading layer comprising a non-fibrous material, and a reagent layer permeable to a substance spreadable within the spreading layer or a reaction product of such a substance, the reagent layer being interposed in the element between the support and the isotropically porous layer.

8. An integral element as described in claim 7 wherein the support transmits electromagnetic radiation of a wavelength within the region between about 200 nm and about 900 nm.

9. An integral element as described in claim 8 and further comprising a reflective layer in fluid contact with and interposed between the spreading layer and the reagent layer.

10. An integral element as described in claim 8 wherein the support is substantially transparent to electromagnetic radiation of a wavelength within the region between about 200 nm and about 900 nm.

11. An integral element as described in claim 10 wherein the reagent layer is of lower permeability to the spreadable substance than is the spreading layer.

12. An integral element for analysis of liquids, said element comprising a support having thereon, in fluid contact, a water-resistant, isotropically porous spreading layer comprising a non-fibrous material, and a reagent layer permeable to substance that is dissolved or dispersed in an aqueous liquid and is spreadable within the spreading layer, said substance comprising a component of the liquid or a reaction product of such a component, the reagent layer being interposed in the element between the support and the isotropically porous layer.

13. An integral element as described in claim 12 wherein the isotropically porous layer is the outermost layer.

14. An integral element as described in claim 12 wherein the support transmits electromagnetic radiation of a wavelength within the region between about 200 nm and about 900 nm.

15. An integral element as described in claim 12 wherein the support is substantially transparent to electromagnetic radiation of a wavelength within the region between about 200 nm and about 900 nm.

16. An integral element as described in claim 12 wherein the reagent layer is of substantially uniform permeability to the dissolved or dispersed substance.

17. An integral element as described in claim 12 wherein the reagent layer comprises a matrix having distributed therein a material interactive with an analyte or a precursor of an analyte or a reaction product thereof to effect a detectable change in the element.

18. An integral element as described in claim 17 wherein the isotropically porous layer contains a surfactant.

19. An integral element as described in claim 17 wherein the isotropically porous layer contains a pigment.

20. An integral element as described in claim 17 wherein the material interactive with an analyte or precursor of an analyte or reaction product thereof is one that, upon such interaction, effects a detectable color change in the element.

21. An integral element as described in claim 17 wherein the support, the isotropically porous layer and the reagent layer transmit electromagnetic radiation of a wavelength within the region between about 200 nm and 900 nm.

22. An integral element as described in claim 17 wherein the reagent layer matrix comprises a hydrophilic colloid.

23. An integral element as described in claim 22 wherein the hydrophilic colloid comprises gelatin, poly(vinylalcohol), agarose, poly(vinyl pyrollidone) or polyacrylamide.

24. An integral element for the analysis of liquids, said element comprising a support that transmits electromagnetic radiation of a wavelength in the region between about 200 nm and 900 nm, said support having thereon, in fluid contact, a water-resistant, isotropically porous spreading layer comprising a blush polymer, and a reagent layer interposed between the isotropically porous layer and the support and comprising a hydrophilic colloid having distributed therein a material interactive with an analyte or a precursor of an analyte or a reaction product of an analyte to effect a detectable change in the element.

25. An integral element as described in claim 24 wherein the blush polymer comprises a cellulose ester, a polycarbonate, a polyurethane, or a polyamide.

26. An integral element as described in claim 24 wherein the isotropically porous layer also comprises a pigment.

27. An integral element as described in claim 24 wherein the reagent layer is of lower permeability to the spreadable substance than is the spreading layer.

28. An integral element as described in claim 24 wherein the isotropically porous layer also comprises a surfactant.

29. An integral element as described in claim 28 wherein the isotropically porous layer also comprises a pigment.

30. An integral element for the analysis of liquids, said element comprising a support that transmits electromagnetic radiation of a wavelength within the region between about 200 nm and 900 nm, said support having thereon, in fluid contact, an isotropically porous spreading layer comprising a pigment, and a reagent layer of lower permeability than said spreading layer, the reagent layer being interposed between the isotropically porous layer and the support and comprising a hydrophilic colloid having distributed therein a material interactiv with an analyte or a precursor of an analyte or a reaction product of an analyte to effect a detectable change in the element.

31. An integral element as described in claim 30 wherein the pigment comprises titanium dioxide or barium sulfate.

32. An integral element as described in claim 30 wherein the isotropically porous layer also comprises a surfactant.

33. An integral element for the analysis of liquids, said element comprising a support that is transparent to electromagnetic radiation of a wavelength within the region between about 200 nm and 900 nm, the support having thereon, in fluid contact, (a) a water-resistant, isotropically porous layer comprising a member selected from the group consisting of a blush polymer, a pigment, a microcrystalline colloid, resinous beads, glass beads and diatomaceous earth, and (b) a reagent layer of lower permeability than said spreading layer, the reagent layer interposed between the support and the isotropically porous layer and comprising a hydrophilic colloid selected from the group consisting of gelatin, polyvinyl alcohol, poly(vinylpyrrolidone) and polyacrylamide and having distributed therein a material interactive with an analyte or a precursor of an analyte or a product of an analyte to effect a detectable change in the element.

34. An integral element as described in claim 33 wherein the blush polymer comprises a cellulose ester, a polycarbonate, a polyurethane, or a polyamide.

35. An integral element as described in claim 33 wherein the support comprises a polymer selected from the group consisting of a cellulose ester, a polycarbonate and poly(ethyleneterephthalate).

36. An integral element as described in claim 33 wherein the interactive material is interactive with glucose and comprises glucose oxidase, peroxidase and either O-dianisidine hydrochloride or 1,7-dihydroxynaphthalene together with 4-aminoantipyrene.

37. An integral element as described in claim 33 wherein the interactive material is interactive with uric acid and comprises copper sulfate and neocuproine.

38. An integral element as described in claim 33 comprising a plurality of reagent layers containing material interactive in the presence of serum glutamic-oxalacetic transiminase or a product thereof, wherein a first reagent layer contains interactive material comprising α-ketoglutarate and aspartate ions and a second reagent layer contains NADH.

39. A method for analysis of liquids comprising
a. applying a liquid sample to an integral element comprising, in fluid contact, an isotropically porous spreading layer comprising a non-fibrous material, and a reagent layer permeable to a substance spreadable within the spreading layer or a reaction product of such a substance, to effect a detectable change in the element in the presence of an analyte and
b. detecting any such change produced in the element.

40. A method as described in claim 39 wherein the sample is applied as a free drop or contact spot.

41. A method as described in claim 39 wherein said change is detected in a region of the element totally within the region of the element in which said change is produced.

42. An integral element for analysis of liquids, said element comprising, in fluid contact, an isotropically porous spreading layer comprising a non-fibrous, isotropically porous material, and a reagent layer permeable to a substance spreadable within the spreading layer or a reaction product of such a substance.

43. An integral element for analysis of liquids, said element comprising a support having thereon, in fluid contact, an isotropically porous spreading layer comprising a non-fibrous, isotropically porous material and a reagent layer permeable to a substance spreadable within the spreading layer or a reaction product of such a substance, the reagent layer being interposed in the element between the support and the isotropically porous layer.

44. An integral element for analysis of liquids, said element comprising a support having thereon, in fluid contact, an isotropically porous spreading layer comprising a non-fibrous material, and a reagent layer of substantially uniform permeability to a substance spreadable within the spreading layer or a reaction product of such a substance, the reagent layer being interposed in the element between the support and the isotropically porous layer.

45. An integral element for analysis of liquids, said element comprising a support having thereon, in fluid contact, a water-resistant, isotropically porous spreading layer comprising a non-fibrous, isotropically porous material, and a reagent layer that is permeable to substance dissolved or dispersed in an aqueous liquid and spreadable within the spreading layer, said substance comprising a component of the liquid or a reaction product of such a component, the reagent layer being interposed in the element between the support and the isotropically porous layer.

46. An integral element for analysis of liquids, said element comprising a support that transmits electromagnetic radiation of a wavelength within the region between about 200 nm and about 900 nm, said support having thereon, in fluid contact, non-fibrous layers comprising an isotropically porous spreading layer, and a reagent layer that is permeable to substance spreadable within the spreading layer or a reaction product of such a substance, the reagent layer being interposed in the element between the support and the isotropically porous layer.

47. An integral element as described in claim 46 wherein the isotropically porous spreading layer is water-resistant and the reagent layer comprises a matrix having distributed therein a material interactive with an analyte or a precursor of an analyte or a reaction product of an analyte to effect a detectable change in the element.

48. An integral element for the analysis of liquids, said element comprising a support that transmits electromagnetic radiation of a wavelength within the region between about 200 nm and about 900 nm, said support having thereon, in fluid contact, an isotropically porous spreading layer comprising a member selected from the group consisting of a blush polymer and particulate matter, and a reagent layer interposed between the isotropically porous layer and the support and comprising a matrix having distributed therein a material interactive with an analyte or a precursor of an analyte or a reaction product of an analyte to effect a detectable change in the element.

49. An integral element as described in claim 48 wherein the particulate matter comprises a member selected from the group consisting of a pigment, a microcrystalline colloid, resinous beads, glass beads and diatomaceous earth.

50. An integral element as described in claim 48 wherein the particulate matter comprises a microcrystalline colloid.

51. An integral element as described in claim 48 wherein the matrix comprises a hydrophilic colloid.

52. An integral element for analysis of liquids, said element comprising a support having thereon, in fluid contact, an isotropically porous spreading layer comprising a non-fibrous material, a reflective layer and a reagent layer, the reflective layer and the reagent layer being permeable to substance spreadable within the spreading layer or a reaction product of such a substance, the reagent layer being interposed between the support and the spreading layer and the reflective layer being interposed between the reagent layer and the spreading layer.

53. A method for analysis of liquids comprising
  a. applying a liquid sample to an integral element comprising (i) a support that transmits electromagnetic radiation of a wavelength within the region between about 200 nm and about 900 nm, and in fluid contact on said support, (ii) an isotropically porous spreading layer comprising a member selected from the group consisting of a blush polymer and particulate matter, and (iii) a reagent layer interposed between the isotropically porous layer and the support, to effect a detectable change in the element in the presence of an analyte and
  b. detecting any such change produced in the element.

54. A method as described in claim 53 wherein said change is detected in the region of the element totally within the region of the element in which such change is produced.

55. A method as described in claim 53 wherein the sample is applied as a free drop or contact spot.

* * * * *

UNITED STATES PATENT AND TRADEMARK OFFICE
CERTIFICATE OF CORRECTION

PATENT NO. : 3,992,158
DATED : November 16, 1976
INVENTOR(S) : Edwin P. Przybylowicz and Allan G. Millikan It is certified that error appears in the above-identified patent and that said Letters Patent are hereby corrected as shown below:

Column 3, line 37, "perferred" should read ---preferred---.

Column 3, line 59, "of a reaction" should read
    ---or a reaction---.

Column 11, line 34, "memebrane" should read ---membrane---.

Column 13, line 31, "adapated" should read ---adapted---.

Column 13, line 66, "elememt" should read ---element---.

Column 14, last line, "eleminating" should read
    ---eliminating---.

Column 15, line 25, "mb/dm$^2$" should read ---mg/dm$^2$---.

Column 16, line 42, "self-suppporting" should read
    ---self-supporting---.

UNITED STATES PATENT OFFICE
CERTIFICATE OF CORRECTION

Patent No. 3,992,158            Dated November 16, 1976

Inventor(s) Edwin P. Przybylowicz et al

It is certified that error appears in the above-identified patent and that said Letters Patent are hereby corrected as shown below:

Column 19, line 45, "interactiv" should read -- interactive --.

Signed and Sealed this

Thirty-first Day of May 1977

[SEAL]

*Attest:*

RUTH C. MASON
*Attesting Officer*

C. MARSHALL DANN
*Commissioner of Patents and Trademarks*